United States Patent [19]

Zartman

[11] Patent Number: 4,677,967

[45] Date of Patent: Jul. 7, 1987

[54] INTRAVAGINAL ANCHOR

[75] Inventor: David L. Zartman, Worthington, Ohio

[73] Assignee: New Mexico State University Foundation, Las Cruces, N. Mex.

[21] Appl. No.: 667,370

[22] Filed: Nov. 1, 1984

[51] Int. Cl.[4] .............................................. A61B 19/00
[52] U.S. Cl. .................................... 128/1 R; 128/130; 128/343
[58] Field of Search ............... 128/130, 131, 129, 128, 128/127, 341, 343, 1 R

[56] References Cited

U.S. PATENT DOCUMENTS

| | | | |
|---|---|---|---|
| 1,863,057 | 6/1932 | Innes | 604/105 |
| 3,192,928 | 7/1965 | Horton | 128/341 |
| 3,397,699 | 8/1968 | Kohl | 604/105 |
| 3,583,389 | 6/1971 | Harvey | 119/1 |
| 3,811,423 | 5/1974 | Dickinson, III et al. | 128/1 R |
| 3,811,424 | 5/1974 | Dickinson, III et al. | 128/130 |
| 4,028,687 | 6/1977 | Hamaguchi et al. | 340/201 R |
| 4,043,338 | 8/1977 | Homm et al. | 604/105 |
| 4,091,807 | 5/1978 | Dickinson, III et al. | 128/130 |
| 4,246,896 | 1/1981 | Horne, Jr. et al. | 128/130 |
| 4,377,157 | 3/1983 | Zartman | 128/130 |
| 4,387,724 | 6/1983 | Zartman | 128/736 |

FOREIGN PATENT DOCUMENTS 981389  1/1965  United Kingdom ................ 128/130

OTHER PUBLICATIONS

"An Automatic System for the Measurement and Recording of Basal Temperature in the Human Female", *Fertility and Sterility*, 15:44–51 (1964), Alvin Singer, M.D. et al.

"Continuously Telemetered Vaginal Temperature in the Baboon", *The Baboon in Medical Research, II*, Ea. H. Vagtborg, University of Texas Press, Austin, pp. 19-35 (1967), A. G. Hendrikx, Ph.D. et al.

"The Detection of Ovulation by Intravaginal Telemetry", *Fertility and Sterility*, vol. 27, No. 9, Sep. 1976, John H. Mattox, M.D. et al.

"Retention Rate in Cows and Heifers of Intravaginal Silastic Coils Impregnated with Progesterone", *J. Reprod. Fert.* (1976), 46, 253-255, by J. F. Roche.

"Contraceptive Effect of Varying Dosages of Progesterone in Silastic Vaginal Rings", *Fertility and Sterility*, (1970), vol. 21, No. 2, pp. 99-103, by Daniel R. Mishell, Jr., M.D., et al.

*Primary Examiner*—Robert Peshock
*Assistant Examiner*—Cary E. Stone
*Attorney, Agent, or Firm*—Lane & Aitken

[57] ABSTRACT

An intravaginal anchoring device for mammalian females comprises an elongated tubular body provided with a plurality of slots disposed substantially parallel to each other and to the length of the tubular body such that, in an expanded position, the ends of the body are moved towards each other and flange portions of the body between adjacent pairs of slots are distended away from an axis of the body and, in a collapsed position, the ends of the body are moved away from each other and the flange portions are retracted towards the axis. The device further comprises a biasing means for urging the body into the expanded position. A purpose of the anchor is to contain any payload appropriate to the interior of a female mammal's vagina.

23 Claims, 3 Drawing Figures

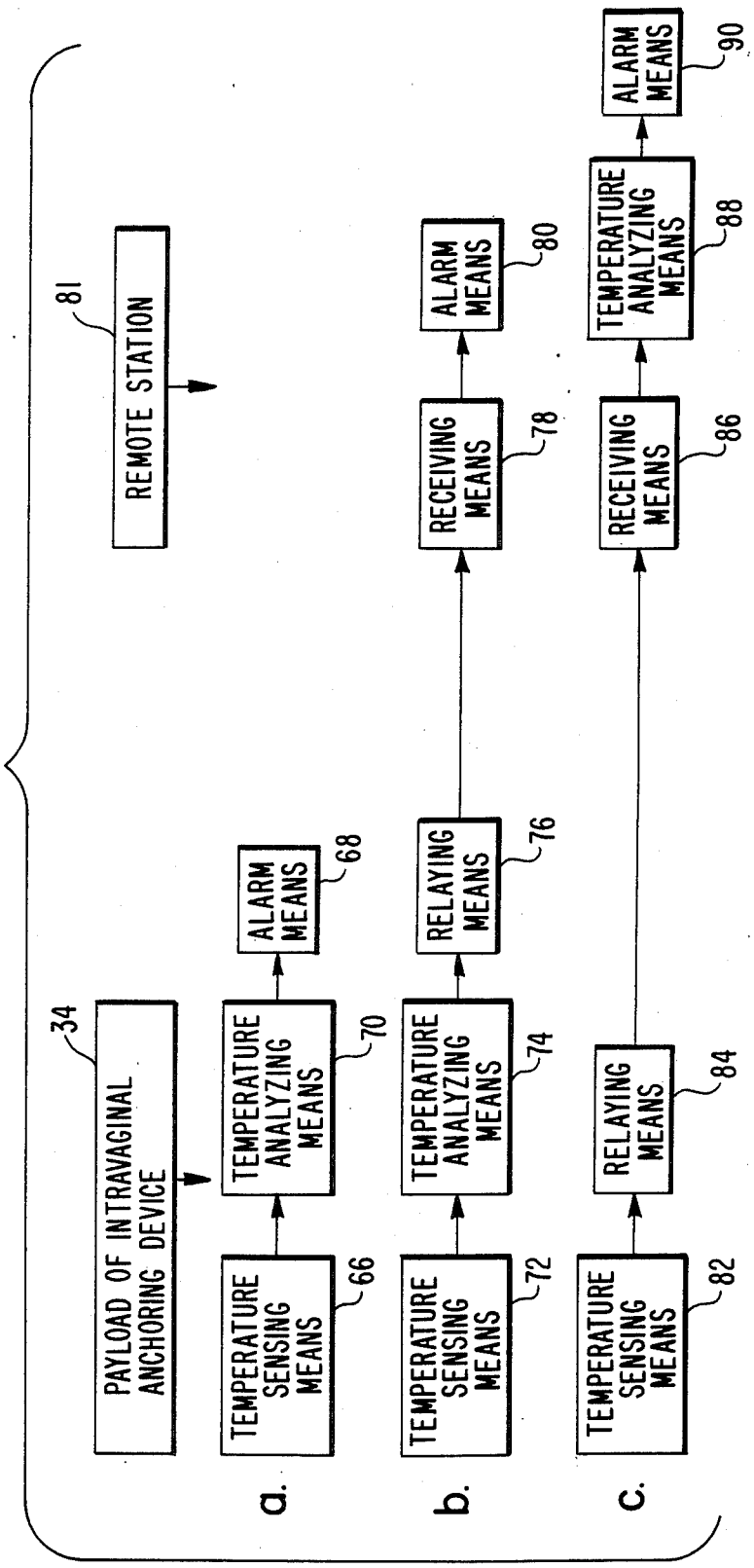

INTRAVAGINAL ANCHOR

BACKGROUND OF THE INVENTION

1. Introduction

This invention pertains to an intravaginal anchoring device that is inserted into the vagina of a mammalian female.

2. Description of the Prior Art

It has been known for some time that the insertion of devices into the reproductive tract of a farm animal can be an effective means to effect changes in biological processes of the animal. An early device commercially available for non-surgical intravaginal implantation is a progesterone-soaked sponge or pessary insert designed for estrus and ovulation control. J. Sreenan, "Retention of Intravaginal Sponge Pessaries by Cattle", *Vet. Rec.* 94:45-47 (1974). Later, a device known as PRID, consisting of rings of Silastic tubing, was used to introduce progesterone into the vagina of a mammalian female by impregnating the rings with progesterone. J. F. Roche, "Retention Rate in Cows and Heifers of Intravaginal Silastic Coils Impregnated with Progesterone", *J. Reprod. Fert.* 46:253-255 (1976). A similar device comprises a vaginal ring formed by covering a stiff metal spring in the form of a closed loop with a silicon polymer. This device is also used to introduce progesterone intravaginally in mammalian females. D. R. Mishell, Jr. et al, "Contraceptive Effect of Varying Dosages of Progestogen in Silastic Vaginal Rings", *Fertility and Sterility* 21:99-103 (1970).

Devices intended for intravaginal implantation are also described in the patent literature. One such device is known commercially as "HEI-GRO" and is disclosed in U.S. Pat. No. 4,091,807. This device is provided with a central shaft that carries axially-spaced mounting rings to which are affixed elongated rods having bulbous ends. The device is inserted intravaginally to stimulate growth. A similar but improved device is disclosed in U.S. Pat. Nos. 4,387,724 and 4,377,157.

U.S. Pat. Nos. 3,811,423 and 3,811,424 disclose a complicated intravaginal anchoring assembly that comprises a plurality of resilient spring-like strands configured in the shape of hoops and disposed around a housing. The strands are mounted in such fashion as to be collapsible under certain conditions, whereupon the device is projected into a sensitive area of the vagina and subsequently expulsed from the animal by peristaltic movement. In one embodiment, the strands are formed into hoops by moving two rings, to which ends of the strands are attached, toward each other, while at the same time preferably rotating one of the rings relative to the other. The duration of the period of retention of the device in an animal's vagina is determined by the contacting and dissolution of an element of the device by ovulation precursive fluids.

Unfortuantely, the intravaginal devices of the prior art have failed to provide an anchoring means that is suitable for use in a variety of applications. In particular, the prior art has failed to provide an intravaginal anchoring device that is easily inserted, appropriately retained for a desired period, and easily removed, and which does not interfere with the normal functioning of the host organ. Further, many of the devices of the prior art are complicated in design and others are unsuitable for accomodating instrument packages that can be applied to identify an animal or monitor or effect biological processes.

Accordingly, it is an object of the present invention to provide an intravaginal anchoring device that is easily inserted into the vagina of a mammalian female and, once inserted, readily retained for the period of retention prescribed in accordance with the particular application for which the device has been inserted, including applications requiring long-term retention.

It is a further object of the invention to provide an intravaginal anchoring device that does not impair the flow of fluids and secretions through the recipient animal's vagina during the period of retention.

It is a further object of the invention to provide an intravaginal anchoring device that is not detrimental to the health of the animal or its natural physiological processes.

It is a further object of the invention to provide an intravaginal anchoring device that does not prevent insemination during the period of retention.

It is a further object of the present invention to provide an intravaginal anchoring device that is capable of carrying an instrument package, a nutriment package, or a medicinal package while being retained in the vagina of a mammalian female.

It is a further object of the invention to provide an intravaginal anchoring device that is capable of carrying an instrument package that is impervious to fluids that are found within the reproductive tract.

It is a further object of the invention to provide an an intravaginal anchoring device that is simple in construction and inexpensive to manufacture.

It is a further object of the invention to provide an intravaginal anchoring device that is relatively small in size, such that is more acceptable and more comfortable for the recipient animal.

It is a further object of the invention to provide an intravaginal anchoring device that is streamlined in construction, such that it is more easily handled, inserted and removed.

It is a further object of the invention to provide an intravaginal anchoring device that maintains a predictable position with the vagina of a mammalian female, such that the antenna of an electronic communications device disposed within an instrument package carried by the device can be optimally disposed relative to an exterior transmitting or receiving station.

It is a further object of the invention to provide an intravaginal anchoring device that is suitable for use in a variety of mammalian females without redesign, but instead by merely altering dimensions of the device.

A still further object of the invention is to provide an intravaginal anchoring device that is easily removed manually or, in certain applications, by natural biological processes such as fetal delivery by the recipient animal, when the prescribed period of retention is intended to be terminated.

Other objectives of the present invention will be apparent from the following detailed description of the preferred embodiments.

SUMMARY OF THE INVENTION

In accordance with the present invention, an intravaginal anchoring device for mammalian females is provided and includes an elongated tubular body that is provided with a plurality of slots disposed substantially parallel to each other and to the length of the body such that, in an expanded position, the ends of the body are moved towards each other and flange portions of the body between adjacent pairs of the slots are distended away from an axis of the body and, in a collapsed position, the ends of the body are moved away from each other and the flange portions are retracted towards the axis. The device is provided with a biasing means for urging the body into the expanded position. A purpose of the anchor is to contain any payload appropriate to the interior of a female mammal's vagina.

DESCRIPTION OF THE PREFERRED EMBODIMENTS

Figure 1:
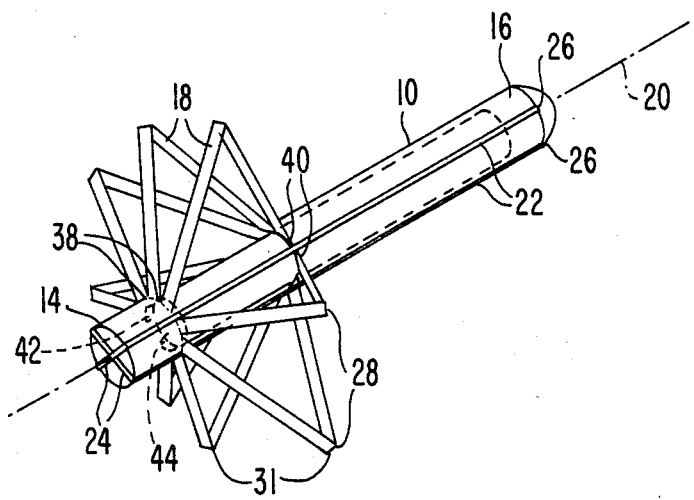
FIG. 1 is a perspective view of a preferred embodiment of the device.

The present invention provides an intravaginal anchoring device that is designed for non-surgical placement in the vagina of any mammalian female, including a human or a bovine, ovine, caprine, equine or porcine animal. It is provided with a cavity that is capable of retaining electronic devices, mechanical devices, medicines and other bio-affecting substances, and other components that are suitably applied to the vagina of a mammalian female. Electronic devices that are suitably carried by the anchor can be used to identify the animal, deter theft, sense and transmit deep body temperature data, sense and transmit biochemical information, sense and transmit information regarding physiological processes, and effect physiological processes of the recipient female or the fetus of the recipient female.

The use of an intravaginally inserted electronic device in the remote sensing and transmitting of the deep body temperature is described in U.S. Pat. No. 4,387,724. The use of such temperature data is very effective in the management of animal reproduction and health. Ovulation is characteristically associated with a temperature spike episode. Irregular reproductive activity can be recognized by processing temperature data over a period of time. Disease and stress impose various kinds of effects on animal temperatures which can be appraised by examining vaginal temperature data profiles. Detection of breeding time, or standing heat, and verification of pregnancy and vaccination is also determinable by evaluating deep body temperature data.

The present invention is also used in conjunction with an electronic device to determine the onset of fetal delivery and related events in the mammalian female. In this application, the intravaginal anchoring device is placed in a mammalian female when breeding age is reached and the device is retained throughout the succeeding months during the breeding period and subsequent pregnancy. At the onset of delivery, the device of the present invention is simply expelled ahead of the fetus, whereupon an abrupt temperature change is sensed by the electronic device which, in turn, generates an alarm signal. The details of the use of the present device in the detection of the onset of delivery and related events is more fully described in the co-pending application of David L. Zartman, entitled "Intravaginal Parturition Alarm and Method for use," which is filed concurrently herewith and hereby incorporated by reference.

The intravaginal anchoring device of the present invention also has therapeutic and health-promoting properties in and of itself. Specifically, the device promotes the production of vaginal mucus. which contains natural immunological agents and white blood cells to combat disease. The increased mucus flow also produces a flushing action on the reproductive tract. The presence of the device, in and of itself, may also directly affect the animal's physiology, for example, through the alteration of hormone production or other biochemical processes, and these changes can be manifest through increased milk production or the like.

Figure 2:
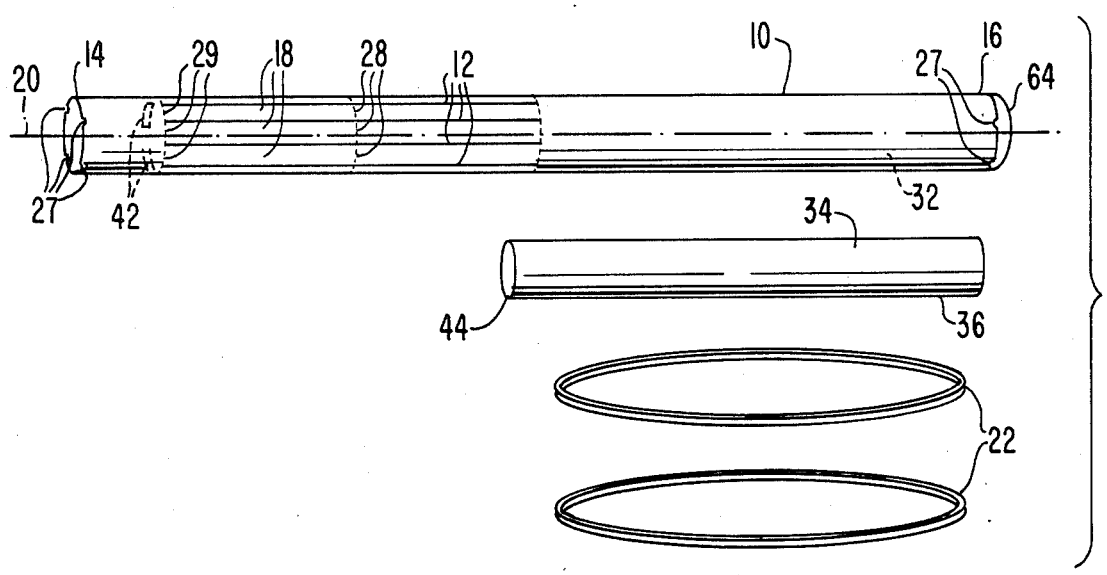
FIG. 2 is a perspective view of unassembled parts of a preferred embodiment of the device.

By reference to the appended drawings, the device will now be more fully described. In the embodiment depicted in the drawings, an elongated tubular body 10 is provided with a plurality of slots 12 that are disposed substantially parallel to each other and to the length of the body. In an expanded position, a first end 14 and second end 16 of the body are moved towards each other and flange portions 18 of the body that are disposed between adjacent pairs of the slots are distended away from a central axis 20, as depicted in FIG. 1, to form a flanged area. In the collapsed position, as depicted in FIG. 2, the ends 14, 16 of the body are moved away from each other and flange portions 18 are retracted towards axis 20.

In the depicted embodiment, a biasing means 22 is provided in the form of elastic bands to urge the body into the expanded position depicted in FIG. 1. Bands 22 are applied by affixing a first end 24 of the bands to end 14 of the body and a second end 26 of the bands to the other end 16 of the body. Notches 27 are provided to retain bands 22 in position. In this fashion, the bands exert a pressure that urges ends 14, 16 of the body together and, at the same time, urges flange portions 18 outwardly. In another embodiment of the invention, the body is constructed in such a fashion to comprise an inherent bias of the body, such that the body naturally assumes the expanded position.

Flange portions 18 are each provided with creases 28, 29, 30 such that, in the expanded position as depicted in FIG. 1, the flange portions are substantially angular in shape, the vertices 31 of the angular shapes being the points most remote from axis 20.

Being of hollow construction, body 10 comprises a cavity 32 adjacent to end 16. Into the cavity is inserted a payload 34 that consists of an instrument package, drugs, medicines, nutrients, minerals, vitamins, and/or other components that are suitably applied to the vagina of a mammalian female. The instrument package may comprise a mechanical instrument means or an electronic instrument means, such as a temperature sensing means. Medicaments and nutrients may be distributed with a medicament or nutrient distribution means. Any other payload appropriate to animal identification, diagnosis, therapy or treatment within the vagina may also be advantageously inserted within the cavity. The payload can be retained within cavity 32 without a separate enclosure, or the payload can be enclosed in a capsule 36 before being inserted into cavity 32. When payload 34 consists of an instrument package, such as electronic instrumentation, it is preferably first enclosed within capsule 36 and sealed, such that the capsule is impervious to fluids found in the vagina. In the event that a capsule 36 is employed, it is retained in cavity 32 by any suitable means, including the use of an adhesive or by rendering the external diameter of capsule 36 slightly larger than the internal diameter of cavity 32, such that capsule 36 exerts a retaining pressure against the walls of cavity 32. If a capsule is not employed, the payload can be directly secured within cavity 32 by similar means.

The intravaginal anchoring device is also provided with a distancing means for maintaining a minimum distance between the ends 38, 40 of the flange portions 18 when the device is in the expanded position as depicted in FIG. 1. In the depicted embodiment, the distancing means comprises capsule 36 which acts as a protrusion extending toward end 14 of the body and at least one stop 42 affixed adjacent ends 38 of flange portions 18. A minimum distance between the ends of the flanges is thereby maintained when end 44 of the capsule rests against stops 42. In another preferred embodiment, the body is constructed in such a fashion as to include an inherent bias, such that the body naturally assumes the configuration depicted in FIG. 1, whereby the minimum distance is substantially maintained without the need of a separate distancing means.

Loop 64 is affixed to an end 16 of the tubular body so that, when inserted, it will be disposed posteriorly in the animal's vagina. The loop facilitates the attachment of a hooked retrieval device when the removal of the anchor is desirable. The provision of a loop is not as important when the recipient animal is a large animal since, in such cases, the anchor can be easily retrieved with a gloved hand.

Figure 3:
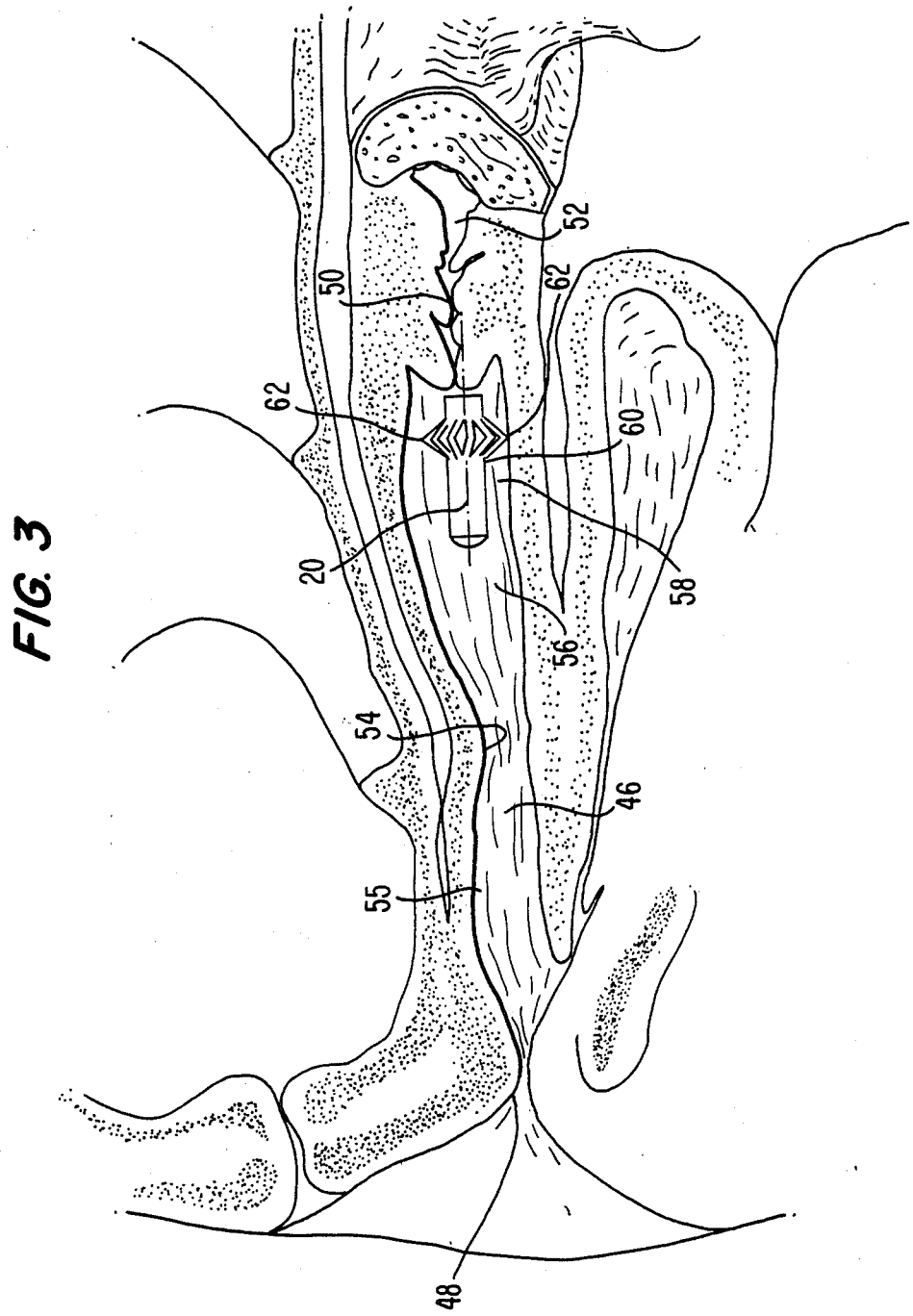
FIG. 3 is a cross-sectional view of a reproductive tract of a mammalian female, depicting the placement of the device therein.

In FIG. 3, the reproductive tract of a cow is depicted prior to the onset of delivery and the positioning of the device is illustrated. In FIG. 3, it is seen that the animal's vagina 46 extends from vulva 48 to cervix 50, which leads to uterus 52. Muscle contractions such as contraction 54 occur within the vagina and it can be seen that posterior portion 55 is generally more tapered than anterior portion 56 prior to the onset of delivery. Deep vagina 58 is located in the anterior portion of the vagina, adjacent to cervix 50. In use, the intravaginal anchoring device 60 is disposed within the vagina in a substantially horizontal position. As will be seen in FIG. 3, the greatest distance between a pair of opposing flange portions 62 is greater than the contracted internal diameter of posterior portion 55 but less than the expanded internal diameter of anterior portion 56, such that both flange portions of an opposing pair of flange portions do not simultaneously exert invasive pressure on interior surfaces of the anterior portion. Thus, the anchoring device of the present invention does not attach or adhere to the anterior portion at all but is instead free and mobile.

The intravaginal anchoring device 60 is essentially retained by muscular contraction of the vagina, particularly in the region 54. Yet, its design is such that peristaltic muscular activity of the vagina is not capable of propelling the device 60 toward and through the posterior portions of the vaginal tract 54 and 55. Only during the act of hard labor and associated relaxation of the pelvis coupled with coincidental hard contractions of vaginal musculature is the intravaginal anchoring device 60 expelled from the anterior vaginal cavity 58.

The intravaginal anchoring device of the present invention is designed for non-surgical placement in the vagina of any mammalian female, including humans and farm animals of the bovine, ovine, caprine, equine or porcine families. The size of the anchor is dictated by the size of the vaginal cavity of the female into which the device is being applied, and this size is dependent upon the age and mammalian family of the animal. The size is selected such that (1) the greatest distance between pairs of opposing, extending flange portions is less than the expanded internal diameter of anterior portion 56 but (2) great enough such that the device does not naturally pass out of the vagina, except in the case of the onset of fetal delivery. This latter feature is established by providing that the greatest distance between pairs of opposing flange portions, in the expanded position, is greater than the interior diameter of posterior portion 55 prior to the onset of fetal delivery as depicted in FIG. 3. Posterior portion 55 expands at the onset of delivery and the greatest diameter between pairs of expanded, opposing flange portions is less than the interior diameter of posterior portion 55 at the onset of delivery such that a parturition alarm can be conveniently provicded, as more fully described in the aforementioned application entitled "Intravaginal Parturition Alarm and Method for Use". Thus, it has been found, for example, that a unit with a tubular body having a length of about 9.5 to 16 cm when compressed and slots of about 4 to 12 cm in length is preferable for cows, heifers and mares, such that the distal vertices of expanded flange portions define a periphery having a diameter of about 6.5 to 9 cm. Such a size has also been used satisfactorily on sows, but units in which the diameter is about 4.5 to 6.5 cm are preferred. A smaller but similarly designed unit is suitable for human females and other small mammals, such as ewes. For humans, a unit having a tubular body and the approximate size of a common tampon, with slots of such length that the distal vertices of expanded flange portions define a periphery having a diameter of about 2.5 cm is satisfactory. In any case, a minimum distance between ends 38, 40 of the flange portions in the expanded position is maintained, and a suitable minimum distance has been found to be about 2 cm.

The anchoring device is composed of a biocompatible material, such as nylon or other non-toxic plastic, that is safe and tissue compatible for live animals. Food grade nylon is a particularly preferred material. The materials of which the device is composed are also preferably easily sterilized by gas, chemicals or irradiation without significantly altering the nature or performance of the anchor.

The anchor can be injection molded or molded in tubular stock with subsequent milling to produce slots to allow the expansion from within of the tubular body to produce the flange portions. The slots are preferably very narrow, such that the flange portions are as wide as possible, but wider slots may be suitable for certain applications. As indicated above, the tubular body will preferably be constructed such that the flange portions 18 naturally assume the expanded position depicted in FIG. 1 and, by virtue of the deformability of the plastic material, are deformable to achieve the collapsed position depicted in FIG. 2.

In a preferred embodiment, capsule 36 is composed of a biocompatible material and is releasably retained within cavity 32 by providing that the exterior diameter of the capsule is slightly larger than the interior diameter of the cavity. In this fashion, capsule 36 can be removed from tubular body 10 after a particular application and disposed of, while the tubular body can be used again, or vice versa. In a particular embodiment, disposable plastic syringes, especially those that have a siliconized interior, are used to encapsulate electronic instruments, whereby the ends of the capsule are heat sealed after the instrument package is loaded.

In order to insert the intravaginal anchoring device, the flange portions are retracted and the device is passed through the vulva and into the vagina. In order to facilitate the insertion of the device in its collapsed position, an apparatus and method such as that described in the co-pending application of David L. Zartman, entitled "Apparatus for Insertion of an Intravaginal Article", field concurrently herewith and hereby incorporated by reference, is employed. Due to the presence of the biasing means that urges the tubular body into the expanded position, the anchoring device assumes the expanded position after insertion into the vagina. When the prescribed period of retention ends, the anchoring device is removed by a gloved hand in the case of larger mammalian animals, or by the attachment of a hook to loop 64, or by the onset of fetal delivery. Due to the flexibility of flange portions 18, the device can be pulled through an area of muscular contraction 54 without difficulty.

It is apparent from the foregoing that the intravaginal anchoring device of the present invention is much improved over the prior art. The anchor of the present invention is easy to insert non-surgically and is designed to fit any mammalian female by simply adjusting the dimensions of the tubular body and the internal capsule. The materials used are safe and tissue compatible for live animals and the anchor does not trap internal secretions or otherwise impair the flow of such secretions. The device does not interfere with copulation, pregnancy, or parturition. It does not cause visible discomfort to the animal after a brief interval following the insertion process, and no physiological processes of the animal have been found to be impaired in any way.

The anchoring device enables deep body placement which is important in the acquisition of deep body temperature data. The retention rate of the anchor is excellent yet removal is accomplished very easily by hand, by a simple retrieval device, or the onset of fetal delivery when removal is intended. Thus, for example, when an instrument package malfunctions, an animal is being disposed of, or an animal is being slaughtered for food purposes, the device is readily removed. In the latter case, the simple operation facilitates the prevention of the device or its contents from accidentally entering into the food chain of humans or pets and prevents damage to food processing machinery. Because the device is relatively small, simple in design, and comprises, in a preferred embodiment, a tubular body of unitary construction, the device is inexpensive. Because of the generally elongated shape of the device, it is naturally held in an animal's vagina in a substantially horizontal position. Such positioning is advantageous because, when the device contains equipment for transmitting or receiving signals in the form of electromagnetic radiation, the antenna of the electronic equipment can be optimally oriented.

EXAMPLE I

In accordance with the present invention, intravaginal anchoring devices were made of food-grade nylon tubular stock having a 2.54 cm outside diameter and a 2.38 cm inside diameter. Longitudinal slots were cut in the tubular stock with a hand tool and spaced apart by 1 cm, so that eight slots were cut and, consequently, eight flange portions were created between the respective pairs of slots. The flange portions were each creased, both at the ends of the flange portions and at the middle of the flange portions in order to provide hinge points for controlled flexibility. When the tubes were compressed longitudinally, the flanges were caused to expand outwardly.

Each of the instrument capsules was made of a disposable 20 cc plastic syringe having an outside diameter that fitted closely into the tubular member, without binding. The piston was drawn from the syringe and the gasket section of the syringe was severed. After loading a temperature sensitive radio transmitter into the barrel of the syringe, the gasket section was inserted into the top of the barrel to enclose the transmitter. Then, the cap portion of the piston was severed and placed over the open end of the barrel, where it was sealed by melting the plastic with a hot wire. Finally, the tip end of the barrel was melted closed with a hot wire. Thus, a completely moisture proof and body-fluid proof capsule was created.

The instrument capsule was loaded into a respective tubular body and notches were cut into either side of the cap and at the other end of the anchor tube. Rubber bands were stretched from notch to notch at each end to create contractile pressure on the anchor. A peg was inserted in the distal end of the tubular body to cause the capsule to be contacted during contraction and thereby arrest the contraction at a distance 2 cm short of complete contraction. This left the flanges partially open and prevented their collapse against the side of the tubular body. A small retrieval loop of stainless steel wire was attached at the distal end of the anchor.

The rubber bands created a flexible contractility so that the flange portions could be retracted as ends of the tubular body were pulled apart. The device was inserted into a cow's vagina through a tube speculum in the collapsed position. Then, as the intravaginal anchoring device was pushed from the anterior end of the speculum with a rod and into the animal's vagina, the flange portions assumed the expanded position so that the anchor was held in the anterior vagina near the cervical wall.

Two anchors were made with an expanded diameter, as measured from the distal vertices of opposing flange portions, of about 15 cm, wherein the slots were 12 cm long. The anchors were placed in the vaginas of two mature Holstein cows, one of which was previously designated as a cull cow and was sick at the time of implantation. This animal had experienced considerable infection and disorder of the reproductive tract following her prior parturition about two months before, and seemed to be nearing death. After one week, the condition of the animal was noticeably improved and the reproductive tract achieved complete normality. As time went on, her condition continued to improve markedly and she came in standing heat. During this period, she did not receive any drugs or medication.

EXAMPLE II

A second intravaginal anchoring device was produced in accordance with Example I, but was modified so that the length of the flange portions was 10 cm. This device was placed in a heifer. The animal was artificially impregnated with the anchor in place and the anchor was retained following impregnation.

EXAMPLE III

In accordance with Example I, an intravaginal anchoring device was prepared in which the flange slots were reduced in length from 12 cm to 4 cm. The length of the tubular stock was correspondingly reduced such that, when compressed, the tubular body continued to have the same overall length of 9.5 cm. The 4 cm models were tested in five cows, three heifers, two sows and eight mares. One cow and one mare were exposed to natural copulation while wearing the anchor with no ill effects being apparent. Three heifers have become pregnant from artificial insemination while wearing the anchor. One sow, one heifer, three cows and seven mares have worn the anchor successfully during the last part of their pregnancies with only one exception. The exception was one mare with a particularly large reproductive tract that expelled the anchor after retaining it for 10 days. It was replaced with an anchor having an 8 cm flange length and this device served perfectly during the 18 remaining days of the mare's pregnancy.

In accordance with the above examples, retention times of over eleven months have been achieved.

It will be apparent to those skilled in the art that many modifications and variations may be introduced without departing from the inventive scope of the present teachings.

I claim:

1. An intravaginal anchoring device for a mammalian female comprising
    (a) an elongated tubular body provided with a plurality of slots disposed substantially parallel to each other and to the length of said body such that, in an expanded position, the ends of said body are moved towards each other and flange portions of said body between adjacent pairs of said slots are distended away from an axis of said body and, in a collapsed position, the ends of said body are moved away from each other and flange portions are retracted towards said axis and
    (b) a biasing means for urging said body into said expanded position,
    wherein, in said expanded position, the greatest distance between distal vertices of opposing flange portions is less than an expanded internal diameter of an anterior portion of said female's vagina but greater than a contracted internal diameter of a posterior portion of said vagina prior to the onset of fetal delivery so that the device is free and mobile therein.

2. The device of claim 1 wherein said biasing means comprises an inherent bias of said body, such that said body naturally assumes said expanded position.

3. The device of claim 1 wherein said flange portions are creased such that, in said expanded position, said flange portions are substantially angular in shape, vertices of said angular shapes being the points most remote from said axis.

4. The device of claim 1, further comprising a distancing means for maintaining a minimum distance between the ends of said flange portions in said expanded position.

5. The device of claim 4 wherein said distancing means comprises an inherent bias of said body such that said body naturally assumes a configuration in which said minimum distance is substantially maintained.

6. The device of claim 1 wherein said body is of unitary construction.

7. The device of claim 1 wherein said body defines a cavity adjacent to at least one end of said body for receiving a payload.

8. The device of claim 7 wherein said payload is disposed within a capsule, said capsule being disposed within said cavity.

9. The device of claim 7 wherein said payload comprises a means for communicating information to or receiving information from outside of said female's vagina while said device is implanted in said vagina.

10. The device of claim 1 wherein, in said expanded position, the greatest distance between distal vertices of opposing flange portions is less than an interior diameter of said posterior portion at the onset of fetal delivery prior to passage of the fetus therethrough.

11. The device of claim 1 wherein, in said collapsed position, the greatest diameter of said device is less than an internal diameter of a posterior portion of said female's vagina prior to the onset of fetal delivery.

12. The device of claim 11 wherein said device defines a cavity for receiving a payload.

13. The device of claim 12 wherein said payload is disposed within said cavity and comprises an instrument means.

14. An intravaginal anchoring device for a mammalian female comprising
    (a) an elongated tubular body provided with a plurality of slots disposed substantially parallel to each other and to the length of said body such that, in an expanded position, the ends of said body are moved towards each other and flange portions of said body between adjacent pairs of said slots are distended away from an axis of said body and, in a collapsed position, the ends of said body are moved away from each other and said flange portions are retracted towards said axis and
    (b) a biasing means for urging said body into said expanded position,
    wherein, in said expanded position, the greatest distance between distal vertices of opposing flange portions is less than an expanded internal diameter of an anterior portion of said female's vagina but greater than a contracted internal diameter of a posterior portion of said vagina prior to the onset of fetal delivery, said biasing means comprising at least one elongated elastic memnber attached at one end to a first end of said body and at the other end to a second end of said body.

15. An intravaginal anchoring device for a mammalian female comprising
    (a) an elongated tubular body provided with a plurality of slots disposed substantially parallel to each other and to the length of said body such that, in an expanded position, the ends of said body are moved towards each other and flange portions of said body between adjacent pairs of said slots are distended away from an axis of said body and, in a collapsed position, the ends of said body are moved away from each other and said flange portions are retracted towards said axis,
    (b) a biasing means for urging said body into said expanded position, and
    (c) a distancing means for maintaining a minimum distance between ends of said flange portions in said expanded position,
    wherein said distancing means comprises a protrusion affixed adjacent to first ends of said flange portions and extending toward second ends of said flange portions and at least one stop affixed adjacent to said second ends of said flange portions, such that said protrusion rests against said stop to maintain said minimum distance.

16. An intravaginal anchoring device for a mammalian female comprising a flexible flanged area capable of assuming an expanded diameter and a collapsed diameter, and a biasing means to urge said area into said expanded diameter, wherein said expanded diameter is less than an expanded internal diameter of an anterior portion of said female's vagina and greater than a contracted internal diameter of a posterior portion of said female's vagina prior to the onset of fetal delivery, such that said device is retained in said anterior portion, and wherein said collapsed diameter is less than said internal diameter of said posterior portion prior to the onset of fetal delivery.

17. The device of claim 16 wherein said expanded diameter is less than an internal diameter of said posterior portion at the onset of fetal delivery prior to the passage of the fetus therethrough.

18. A method of anchoring a device within an anterior portion of the vagina of a mammalian femal comprising the steps of
   selecting an anchor having an elongated tubular body provided with a plurality of slots disposed substantially parallel to each other and to the length of said body such that, in an expanded position, the ends of said body are moved towards each other and flange portions of said body between adjacent pairs of said slots are distended away from an axis of said body and, in a collapsed position, the ends of said body are moved away from each other and said flange portions are retracted towards said axis, and a biasing means for urging said body into said expanded position, wherein, in said expanded position, the greatest distance between distal vertices of opposing flange portions is less than an expanded internal diameter of an anterior portion of said female's vagina but greater than a contracted internal diameter of a posterior portion of said vagina portion to the onset of fetal delivery,
   configuring said body into said collapsed position,
   inserting said body through said contracted internal diameter and into said anterior portion,
   expanding said body into said expanded position, and
   biasing said body into said expanded position such that said anchor is retained within said anterior portion.

19. The method of claim 18 wherein said configuring step comprises the steps of simultaneously moving the ends of said body away from each other and retracting said flange portions towards said axis.

20. The method of claim 18 wherein said expanding step comprises the steps of simultaneously moving the ends of said body towards each other and distending said flange portions away from said axis.

21. The method of claim 18 wherein said inserting step comprises the steps of inserting said anchor through a tube speculum in said collapsed position.

22. The method of claim 18 wherein said biasing step comprises the step of allowing said body to assume a naturally expanded position.

23. A method of anchoring a device within an anterior portion of the vagina of a mammalian female comprising the steps of
   selecting an anchor having an elongated tubular body provided with a plurality of slots disposed substantially parallel to each other and to the length of said body such that, in an expanded position, the ends of said body are moved towards each other and flange portions of said body between adjacent pairs of said slots are distended away from an axis of said body and, in a collapsed position, the ends of said body are moved away from each other and said flange portions are retracted towards said axis, and a biasing means for urging said body into said expanded position, wherein, in said expanded position, the greatest distance between distal vertices of opposing flange portions is less than an expanded internal diameter of an anterior portion of said female's vagina but greater than a contracted internal diameter of a posterior portion of said vagina prior to the onset of fetal delivery,
   configuring said body into said collapsed position,
   inserting said body through said contracted internal diameter and into said anterior portion,
   expanding said body into said expanded position, and
   biasing said body into said expanded position such that said anchor is retained within said anterior portion, said biasing step comprising the step of affixing at least one elongated elastic member to both ends of said body.

* * * * *